United States Patent
Salvador

(10) Patent No.: US 8,455,461 B2
(45) Date of Patent: *Jun. 4, 2013

(54) COMPOSITIONS CONTAINING A SYNERGIC MIXTURE OF POLYOLS AND XYLOGLUCANES AS PHYTOSANITARY AND BIO-FERTILISING PRODUCTS

(75) Inventor: Pascal Salvador, Grenoble (FR)

(73) Assignee: Elicityl, Crolles (FR)

( * ) Notice: Subject to any disclaimer, the term of this patent is extended or adjusted under 35 U.S.C. 154(b) by 291 days.

This patent is subject to a terminal disclaimer.

(21) Appl. No.: 12/674,789

(22) PCT Filed: Jul. 9, 2008

(86) PCT No.: PCT/FR2008/001000
§ 371 (c)(1),
(2), (4) Date: Mar. 25, 2010

(87) PCT Pub. No.: WO2009/043984
PCT Pub. Date: Apr. 9, 2009

(65) Prior Publication Data
US 2010/0210463 A1      Aug. 19, 2010

(30) Foreign Application Priority Data

Jul. 19, 2007   (FR) ...................................... 07 05238

(51) Int. Cl.
*A61K 31/715* (2006.01)
*A61K 31/716* (2006.01)
(52) U.S. Cl.
CPC .............. *A61K 31/716* (2013.01); *A61K 31/715* (2013.01)
USPC ............................................................ 514/54
(58) Field of Classification Search
None
See application file for complete search history.

(56) References Cited

U.S. PATENT DOCUMENTS

| | | | |
|---|---|---|---|
| 6,331,504 B1 * | 12/2001 | Balsevich | ..................... 504/100 |
| 2004/0023924 A1 | 2/2004 | Lienart | |
| 2005/0153933 A1 * | 7/2005 | Lienart et al. | ..................... 514/61 |
| 2005/0268359 A1 * | 12/2005 | Mach et al. | ..................... 800/298 |
| 2007/0065388 A1 * | 3/2007 | Miyamoto et al. | ......... 424/70.13 |
| 2009/0018020 A1 | 1/2009 | Lienart et al. | |

FOREIGN PATENT DOCUMENTS

| | | |
|---|---|---|
| WO | 95/28836 | 11/1995 |
| WO | 02/26037 | 4/2002 |
| WO | 03/079785 | 10/2003 |

OTHER PUBLICATIONS

Valliyodan et al.; "Understanding regulatory networks and engineering for enhanced drought tolerance in plants"; 2006; Current Opinion in Plant Biology; 9:1-7.*

Valliydodan et al., "Understanding regulatory networks and engineering for enhanced drought to tolerance in plants", Current Opinion in Plant Biology, Quadrant Subscription Services, GB, vol. 9, No. 2, Apr. 2006, XP005306212, ISSN: 1369-5266, pp. 189-195.

International Search Report dated Feb. 27, 2009, from corresponding PCT application.

* cited by examiner

*Primary Examiner* — Timothy Thomas
(74) *Attorney, Agent, or Firm* — Young & Thompson

(57) ABSTRACT

A eliciting composition including a synergistic mixture of at least one xyloglucan derivative and at least one polyol.

3 Claims, No Drawings

COMPOSITIONS CONTAINING A SYNERGIC MIXTURE OF POLYOLS AND XYLOGLUCANES AS PHYTOSANITARY AND BIO-FERTILISING PRODUCTS

A subject of the present invention is novel compositions based on xyloglucans and polyols and their use in the phytosanitary and biofertilization fields.

The cell walls of fruits and vegetables are formed by polysaccharides, mainly pectin, cellulose and xyloglucan which are involved in putting the walls in place (Levy S et al., Plant J. 1997, 11(3): 373-86). Xyloglucan is also found in large quantities in the endosperm of the seeds of Dicotyledons.

Xyloglucan is a 1,4-β-glucan polymer substituted differently according to its origin. In the Dicotyledons, the substitutions of the linear 1,4 β-D-glucan chains most often involve 1,6 α-D-xylosyl-, or 1,6 α-D-xylose 1,2 β-D-galactosyl-type branchings, and fucose can be associated, at the terminal position, with galactose, i.e. a 1,6 α-D-xylose 1,2 β-D-galactose 1,2 α-L-fucosyl-type side branching. In the Dicotyledons, the fucose residue is always absent from the endosperm, and it can be replaced by the α-L-arabinose residue, for example in certain Solanaceae. The xyloglucan of Monocotyledons differs from that of Dicotyledons by a lower rate of substitution by xylose and galactose residues and by the absence of fucose. The xyloglucan forms, with the cellulose microfibres, bridged structures which constitute the structure and ensure the flexibility of the cell wall of plants (Pauly M, Albersheim P, Darvill A, York W S (1999) Plant J, 20 (6): 629-39).

Xyloglucan is a substrate of endoxyloglucanases (Vincken J P, Beldman G, Voragen A G Carbohydr Res (1997) 13, 298(4):299-310) or of xyloglucan endotransglycosylase (Steele N M, Fry S C, Biochem J (1999) 15, 340, 1, 207-211), namely of enzymatic activities capable of modifying the structure of the cell walls during cell elongation, in the germination and fructification periods for example and which are dependent on hormones, in particular auxins (Hetherington P R and Fry S. (1993) Plant Physiology, 103, 987-992), and gibberellins (Maclachlan G and Brady C (1994) Plant Physiol 105, 965-974).

Xyloglucan, in particular a fucosylated oligomer, the nonasaccharide XXFG (described in Fry et al. (1993) Physiologia Plantarum, 89, 1-3), is well known for its anti-auxinic effect (McDougall CJ and Fry S C (1989) Plant Physiol 89, 883-887). Conversely, oligomers without fucose but with galactose such as the oligomers XXLG and XLLG have an auxinic effect (McDougall GJ and Fry S C (1990) Plant Physiology 93, 1042-1048).

Moreover, a number of signals generate activated oxygen species (also referred to as "oxidative burst"). Active oxygen species are well known for being released during plant-pathogen interactions. Oligosaccharides of various origin (polygalacturonic acid, chitosan, O-glycans etc.) have been recorded for their ability to generate an oxidative burst (Low P S and Heinstein P F (1986) Arch. Biochem. Biophys. 249, 472-479; Rogers K R., Albert F, and Anderson A J (1988) Plant Physiol 86, 547-553; Apostol I, Heinstein P F and Low P S (1989) Plant Physiol 90, 109-116; Vera-Estrella R, Blumwald E and Higgins V J (1992) Plant Physiol. 1208-1215; Bolwell G P, Butt V S, Davies D R and Zimmerlin A. (1995) Free Rad. Res. Comm 23, 517-532; Orozco-Cardenas M and Ryan C A (1999) PNAS, 25, 96, 11, 6553-655; Nita-Lazar M, Iwahara S, Takegawa K, Lienart Y (2000) J Plant Physiol, 156, 306-311). Oxidoreductase NAD(P)H enzymes for the release of superoxide anion (Van Gestelen P V, Asard A, Caubergs R J (1997) Plant Physiol 115, 543-550) and peroxidases for the formation of peroxide or of superoxide anion or of OH radicals are involved (Baker C J and Orlandi E W (1995) Ann. Rev. Phytopathol, 33, 299-321; Chen S X and Schopfer P (1999) Eur Bioch 260, 726-735). Other signals (salicylic acid, jasmonates, cGMP, NO etc.) also generate a burst (Chen Z, Malamy J, Henning J, Conrath U, Sanchez-Casas P, Silva H, Ricigliano J, Klessig D F (1995) Proc Natl Acad Sci USA, 92, 4134-4137; Voros K, Feussner I, Kuhn H, Lee J, Graner A, Lobler M, Parthier B, Wasternack C Eur J Biochem (1998) 15, 251, 36-44; Durner J, and Klessig J, Wendehenne D, Klessig D F (1998) Proc Natl Acad Sci USA, 95, 10328-10333; Durner D and Klessig D F (1999) Current Opinion in Plant Biology, 2, 369-374).

Extreme environmental conditions (drought, cold, UV, salinity etc.) trigger the same effect (Suzuki N, Mittler R (2006) Physiol. Plant. 126, 45-51; Wang, W., Vinocur, B., Altman, A. (2003) Planta 218 1-14; Palva, E. T., Htiharju, S. T., Tamminen, I., Puhakainen, T., Laitinen, R. Savensson, J., Helenius, E., and Heino, P. (2002) JIRCAS working report 9-15).

The major role of $H_2O_2$ in the generation of the burst as in the regulation of oxidative stress is based on:
- its formation by dismutation from the superoxide anion (Bolwell G P, Davies D R, Gerrish C, Auh C K and Murphy T M (1998) Plant Physiol 116, 1379-1385),
- its use in $C_{18}$ fatty acid metabolism sequences (for the peroxidation of lipids (Koch E, Meier B M, Eiben H-G, Slusarenko A (1992) Plant Physiol 99, 571-576) or for the synthesis of octadecanoids and of their derivatives, certain of which such as the methyl-jasmonates are metabolites with a hormonal function,
- its function as substrate for the peroxidase and catalase enzymes, property of limiting the accumulation of toxic peroxide for the cell (Baker C J, Harmon G L, Glazener J A and Orlandi E W (1995) Plant Physiol, 108, 353-359).

The active oxygen species, the superoxide anion in particular, control different metabolic pathways. They are involved in:
- the biosynthesis of polyamines: monoamines are oxidized to aldehydes with the production of $NH_3$ and peroxide. The oxidation of L-arginine by nitrite synthase results in the formation of a polyamine precursor (L-citrulline),
- the synthesis of ethylene,
- the synthesis of gibberellins More than 20 oxidases are involved in the regulation of the biosynthesis of gibberellins.

The active oxygen species are involved in signal transduction stages, because they are associated with receptor bond activity or transduction enzyme activity (Jabs T, Tschope M, Colling C, Hahlbrock K and Scheel D (1997) Proc Natl Acad Sci USA 29, 94, 9, 4800-4805; Durner J, Wendehenne D, Klessig D F (1998) Proc Natl Acad Sci USA, 95, 10328-10333).

They are involved in the regulation of the cell redox potential using thiol groups (GSSG-GSH, cystine-cysteine conversion, etc.). In this way, they control senescence processes which are manifested during certain flowering and fructification phases in different organisms.

The oxidative burst interferes with the hormonal metabolism, the most efficient potential for regulating the flowering and fructification stages (in particular their triggering and their duration are programmed by a hormonal balance (auxin/cytokinin ratio for example), and the active oxygen species, including peroxide, control the synthesis of polyamines).

In the applications WO 02/26037 and WO 03/079785 the Inventors described that xyloglucan polymers and oligomers, in particular compounds comprising an osidic structure of formula XFG, as well as compounds derived from the latter, have a stimulating effect on the glutathione reductase enzyme, the phospholipase D enzyme in plants, as well as the glycosylhydrolases.

By stimulating the glutathione reductase enzyme, the compounds of the invention trigger the reactions of adaptation to any oxidant stress, such as cold in particular, by limiting the toxic effects of the active oxygen species (Allen R D, Webb R P, Schake I T S (1997) Free Radic Biol Med, 23 (3):473-479; O'Kane D, Gill V, Boyd P, Burdon R (1996) Planta, 198 (3):371-377), and they regulate the redox potential of the cell, which modifies the activity of enzymes or thiol-dependent proteins, phospholipase D, thiol-proteases and inhibitors of thiol-proteases in particular (Taher M M, Mahgoub M A, Abd-Elfattah (1998) AS Biochem Mol Biol Int 46 3, 619-28), as well as by a thiol-dependent protease inhibitor induction effect, and without however activating a cascade of other enzymatic systems in proportions harmful to the plant.

By stimulating the phospholipase D activity, these compounds amplify the hormonal effect of abscisic acid to the extent that the activation of the enzyme leads to the production of phosphatidic acid (which mimics the effects of abscisic acid). In this way, they can reveal an antagonism against the gibberellins, ethylene or jasmonates (Grill E., Himmelbach A. (1998) Current Opinion in Plant Biology, 1, 1, 5, 412-418; Ritchie S, Gilroy S (1998) Plant Biology, 95, 5, 3, 2697-2702; Moons A, Prinsen E, Bauw G, Van Montagu M (1997) Plant Cell 9 12, 2243-59). These compounds have been found to be particularly useful in the phytosanitary and biofertilization field, in particular as elicitors, and more particularly to combat abiotic stress in plants, and control flowering and fructification.

In fact at present, apart from chemical fertilizers, the control of vegetable development is based mainly on:
  the use of agricultural compositions enriched with trace elements, with nitrate, phosphate, and potassium components, polyamines or certain hormones,
  the use of natural or genetically modified micro-organisms, which improve the quality of the soil, promoting vegetable growth or increasing crop yield; these are in particular the Rhizobiaceae such as R. meliloti and B. japonicum, free-nitrogen-fixing bacteria, such as Bacillus and Pseudomonas, and fungi such as Penicillium,
  the development of transgenic plants. This technology has come up against legal problems and strong opposition on the part of consumers; moreover, it has not yet resulted in satisfactory uses in the biofertilizer sector.

A need still exists in this field to find means for controlling plant development which are effective and not toxic for the plants.

In the pursuit of their work, the inventors have demonstrated that sorbitol has a synergistic effect on the eliciting effects of XFGol, one of the xyloglucans described in the international applications WO 02/26037 and WO 03/079785.

Sorbitol is especially known for these uses in the agri-food industry (as an artificial sweetener), in medicine (as a medicament for treating constipation, due to its laxative effect) and in cosmetics (as a moisturizer and thickening agent). In agriculture, sorbitol is used as an additive in phytosanitary formulations.

One of the purposes of the present invention is to provide novel eliciting compositions characterized in that they include a synergistic mixture of at least one xyloglucan derivative and at least one polyol.

Within the meaning of the present invention, by xyloglucan is meant polymers of 1,4-β-glycan substituted by 1,6-α-xylosyl or 1,2-β-galactosyl type groups, in particular the derivatives described by Fry et al. (1993) Physiologia Plantarum, 89, 1-3 and by the inventors in the international applications WO 02/26037 and WO 03/079785.

In an advantageous embodiment of the invention, the at least one xyloglucan derivative corresponds to the formula:

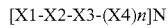

in which
  X1, X2, X3, and X4, independently of each other, represent a monosaccharide chosen from glucose, galactose, xylose, fucose and arabinose, this monosaccharide being if appropriate in reduced form and/or being substituted, in particular by a $C_1$-$C_4$ alkyl or acyl group, such as a methyl or acetyl group, X1, X2, X3, and X4, independently of each other, being if appropriate substituted by one or more monosaccharides chosen from glucose, galactose, xylose, fucose and arabinose, and/or by one or more monosaccharide chain formations of formula X5-X6-(X7)m, in which X5, X6, and X7, independently of each other, represent a monosaccharide chosen from glucose, galactose, xylose, fucose and arabinose, and m represents 0 or 1, or a compound derived from those defined above, in particular by modification or substitution of one or more abovementioned monosaccharides,
  n represents 0 or 1 and
  N represents an integer comprised between approximately 50 and approximately 300, advantageously comprised between approximately 50 and approximately 100, in the case of polymers and represents an integer comprised between approximately 1 and approximately 50, advantageously comprised between approximately 2 and approximately 50, even more advantageously comprised between approximately 2 and approximately 20, in particular between 5 and 12, in the case of oligomers.

Even more advantageously, the at least one xyloglucan polymer is a compound A which comprises:
  one or two X chain formations, X being chosen from the group constituted by the following chain formations:
    α-D-Xylopyranosyl(1,6)-β-D-Glucopyranosyl,
    α-D-Xylopyranosyl(1,6)-D-Glucopyranose,
    β-D-Xylopyranosyl(1,4)-β-D-Glucopyranosyl and
    β-D-Xylopyranosyl (1,4)-D-Glucopyranose,
  or a reduced form of X, also denoted Xol,
  one or two F chain formations, F being chosen from the group constituted by the following chain formations:
    α-L-Fucopyranosyl(1,2)-β-D-Galactopyranosyl,
    (1,2)-α-D-Xylopyranosyl(1,6)-β-D-Glucopyranosyl,
    α-L-Fucopyranosyl(1,2)-β-D-Galactopyranosyl,
    (1,2)-α-D-Xylopyranosyl(1,6)-D-Glucopyranose,
    α-L-Fucopyranosyl(1,2)-β-D-Galactopyranosyl(1,2)-
      β-D-Xylopyranosyl(1,4)-β-D-Glucopyranosyl and
    α-L-Fucopyranosyl(1,2)-β-D-(1,2)-β-D-Xylopyranosyl(1,4)-D-Glucopyranose,
  or a reduced form of F, also denoted Fol, and
    at least one G chain formation, G being chosen from the group constituted by the following units:
    β-D-glucopyranosyl and
    D-Glucopyranose,
  said units being optionally substituted in position 4,
  or a reduced form of G, also denoted Gol,
  said X, F and G chain formations being linked to each other in a random order, and comprising, if appropriate, the following modifications: (i) by modification of hydroxyl groups, namely acetylated or methoxylated or acylated derivatives, the glucose residue in the terminal position of which is reduced or not, (ii) by modification of the reducing terminal unit, such as by reductive amination, (iii) by oxidation, in position 6 of the accessible Gal and Glc residues.

In the context of the present invention, the following abbreviations are used: Fuc for fucose, Gal for Galactose, Glu for glucose, Xyl for xylose, Xol, Fol and Gol respectively for the reduced forms of X, F and G and correspond to those used by Fry et al. (1993) Physiologia Plantarum, 89, 1-3.

Advantageously the compounds A are chosen from the group comprising the following formulae:

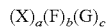

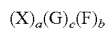

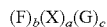

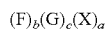

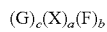

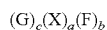

in which:
G, X and F are as defined previously and a, b, and c, independently of each other represent 1, or 2.

Even more advantageously, in the eliciting compositions according to the invention, the compound A is chosen from the group comprising XFG, FXG, FGX, GFX, and GXF, the glucose residue in the terminal position of which is reduced or not, or comprising structures derived by modification as defined previously or from the group comprising: XGXG, XFGX, FGXX, FXGX, DOW, GXXF, GXFX, GFXX, XXGF, XGXF, XGFX and XXFG.

Among the compounds XFG or its derivatives there may in particular be mentioned:

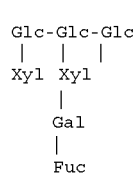
XFG

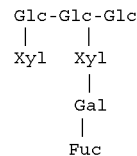
XGF

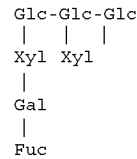
FXG

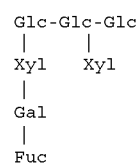
FGX

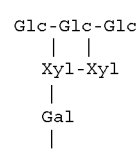
GFX

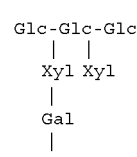
GXF the glucose residue in the terminal position of said compounds being reduced or not, or comprising structures derived by modification as defined above.

In a particularly advantageous embodiment of the invention, compound A corresponds to the following formula (I):

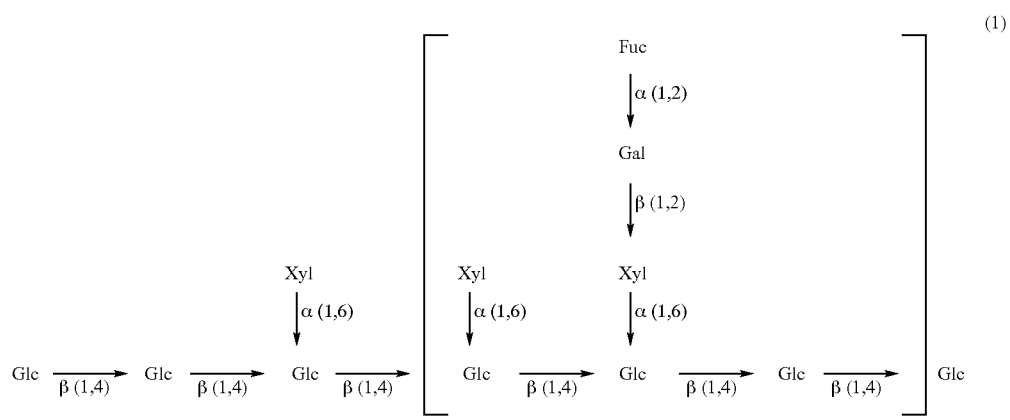

in particular to the following formula XFG:

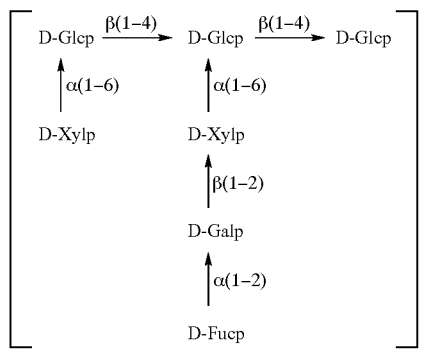

or to the following formula XFGol:

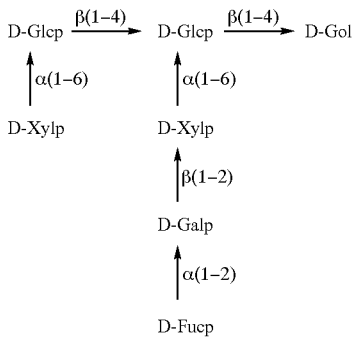

In an embodiment of the invention which is also advantageous, the at least one polyol is chosen from the group comprising sorbitol, mannitol, xylitol, ethylene glycol, glycerol or glycerine, polyethylene oxide or polyethylene glycol, polypropylene glycol and polytetramethylene glycol.

A subject of the present invention is also an eliciting composition characterized in that it comprises a synergistic mixture of XFGol (heptamaloxyloglucan CAS Number 870721-81-6) combined with sorbitol.

According to the invention, the polyol represents between 0.01 and 1% of the composition, advantageously between 0.05 and 0.5%, even more advantageously between 0.08 and 0.15% and the xyloglucan derivative is present in a concentration comprised between 0.1 nM and 1 µM, advantageously in a concentration comprised between 1 and 500 nM A subject of the invention is also a process for the adaptation of plants to abiotic stress, in particular adaptation to the cold, or to water stress, characterized in that it comprises a stage of treatment of the plants with a synergistic composition according to the invention, in particular by irrigation of the soil in which these plants are cultivated, with a composition comprising said compound, or by coating the seeds with such a composition, or by foliar spraying of such a composition in the field, onto the plants to be treated.

The compositions according to the invention are particularly suited to increasing the resistance of vines to the frost.

A subject of the invention is also a process for the control of flowering, and more particularly a process for the control of floral induction, flowering duration, and flower abscission, and/or for the implementation of a process for the control of plant fructification, and more particularly of a process for the control of the triggering and duration of fruit maturation, leaf and fruit abscission characterized in that it comprises a stage of treatment of the plants with a composition according to the invention.

A subject of the invention is also a process for the stimulation of the production of glycosylhydrolases in plants, characterized in that it comprises a stage of treatment of the plants with a composition according to the invention, in particular by irrigation of the soil in which these plants are cultivated, with a composition comprising said compound, or by coating the seeds with such a composition, or by foliar spraying of such a composition in the field, onto the plants to be treated.

A subject of the invention is also a process for the induction of defence reactions in the plants against pathogens characterized in that it comprises a stage of treatment of the plants with a composition according to the invention, in particular by irrigation of the soil in which these plants are cultivated, with a composition comprising said compound, or by coating of the seeds with such a composition, or by foliar spraying of such a composition in the field, onto the plants to be treated.

A subject of the invention is also the use of sorbitol for increasing the eliciting power of the xyloglucans in a composition intended to be applied to the plants.

By control of flowering is meant more particularly control of the key phases of the flowering process such as antheresis (Wang M, Hoekstra S, van Bergen S, Lamers G E, Oppedijk B J, Heijden M W, de Priester W, Schilperoort R A (1999) Plant Mol Biol 39, 3:489-501), or the development of flower buds (Lim C O, Lee I F, Chung W S, Park S H, Hwang I, Cho M J (1996), Plant Mol Biol, 30, 2, 373-379), such as the floral induction or abscission phases (Colasanti J, Sundaresan V (2000) Trends Biochem Sci, 25, 5, 236-240.

By control of fructification is meant more particularly control of the triggering and/or duration of the maturation phase (Fan L, Zheng S, Wang X (1997) Plant Cell, 9, 12, 2183-9; Ryan S N, Laing W A, Mc Canus M T (1998), Phytochemistry, 49, 4, 957-963), control of cell wall metabolism with respect to the accumulation of sugars and phenols (Fillion L, Ageorges A, Picaud S, Coutos-Thevenot P, Lemoine R, Romieu C, Delrot S (1999) Plant Physiol 120 (4):1083-94), and control of leaf and fruit abscission (Gomez-Cadenas A, Mehouachi J, Tadeo F R, Primo-Millo E, Talon M (2000), Planta, 210, 4, 636-643).

The induction of defence reactions against pathogens is, with respect to the elicitation of PR-proteins, in particular of the enzymes 1,3-β D glucanase and endochitinase, also known to be involved in plant development (Munch-Garthoff S, Neuhaus J M, Boller T, Kemmerling B, Kogel K H (1997) Planta 201, 2, 235-44; Buchter R, Stromberg A, Schmelzer E, Kombrink E (1997) Plant Mol Biol 35, 6, 749-61; Robinson S P, Jacobs A K, Dry I B (1997) Plant Physiol 114, 3, 771-8).

The control of metabolic and catabolic modifications of which certain tissues are the object in differentiation or senescence periods, is in accordance with the elicitation of the enzymes 1,4-β-D-glucanase and β-D-xylosidase (Trainotti L, Spolaore S, Ferrarese L, Casadoro G (1997) Plant Mol Biol 34 (5):791-802; Kalaitzis P, Hong S B, Solomos T, Tucker M L (1999) Plant Cell Physiol 40(8), 905-8).

Advantageously, the compositions according to the invention are presented as agricultural inputs in solid form (in particular powder, granules, pellets), or in liquid form (in particular in aqueous solution), combined or not combined with other agricultural input compounds.

Among the plants capable of being treated within the scope of the present invention, can there can mainly be mentioned agronomically useful plants, such as the vine, fruit trees (in particular kiwi, apple, pear, walnut), grasses such as turf, cereals (in particular rice, barley), oleaginaceous plants (in particular soya, rape, sunflower), protein plants (in particular peas), and market garden crops (in particular tomatoes)).

The following example illustrates the invention.

EXAMPLE

Improvement of the Frost-Resistance of Young Vine Plants

1.1. Operating Method

Plants originating from different vine varieties: the Chardonnay and Cabernet-Sauvignon varieties are used. Each sample, composed of 5 to 21 plants, is treated by foliar spraying at different vegetative stages on the BBCH scale with a mixture containing the xyloglucan elicitor, heptasaccharide XFGol or heptamaloxyloglucan, in solution at variable doses combined or not combined with sorbitol; the spraying of 2.5 ml of solution per plant is carried out using a sprayer (deviation of +/−1%).

After use of the elicitor, the plants were exposed to cold stress of variable intensity and duration. After exposure to the cold, the plants are placed in a climatic chamber at 20° C. with a 12-hour day/night alternation. The appearance of the leaves is observed 24 hours and 72 hours after removal from the cold. The effects of the cold are evaluated by observing the foliar necroses induced by frost and the plants are kept for several months in order to monitor their subsequent development.

The results are expressed by the protection index c (%)=100−P; P, being the proportion of foliar necroses.

The results are also expressed in gain:

$$\text{Gain} = \frac{(I_f \text{ Elicited} - I_f \text{ Control})}{I_f \text{ Control}} \text{ expressed in \%}$$

1.2. Results

These are given in Tables 1 to 3.

In the case of Chardonnay, the mixture containing 5 nM of heptamaloxyloglucan as elicitor and 0.1% sorbitol induces a frost protection which is always greater than that obtained with a mixture containing the elicitor alone (Table 1). On the other hand, the 0.1% sorbitol is without effect when the elicitor itself has no effect.

TABLE 1

Effects on Chardonnay

| | | All physiological stages combined | | |
|---|---|---|---|---|
| | Dry Control | 0.5 nM Elicitor + 0.1% sorbitol | 5 nM Elicitor | 5 nM Elicitor + 0.1% sorbitol |
| $I_f$% | 54 | 17 | 40 | 85 |
| average number of plants | 13 | 9 | 5 | 13 |
| Gain % | — | 0 | 0 | 57 |

In the case of Cabernet-Sauvignon the 0.1% sorbitol is without effect when the elicitor itself has no effect (Table 2). The mixture containing 500 nM of heptamaloxyloglucan as elicitor and 0.1% sorbitol induces frost-protection which is always greater than that obtained with a mixture containing the elicitor alone (Tables 2 and 3).

TABLE 2

Effect on Cabernet-Sauvignon (first series)

| | | All physiological stages combined | | |
|---|---|---|---|---|
| | Dry control | 50 nM Elicitor + 0.1% sorbitol | 250 nM Elicitor + 0.1% sorbitol | 500 nM Elicitor + 0.1% sorbitol |
| $I_f$% | 29 | 33 | 30 | 56 |
| average number of plants | 21 | 6 | 10 | 16 |
| Gain % | — | 17 | 5 | 97 |

TABLE 3

Effect on Cabernet-Sauvignon (second series)

| | | All physiological stages combined | |
|---|---|---|---|
| | Dry control | 500 nM Elicitor | 500 nM Elicitor + 0.1% sorbitol |
| $I_f$% | 20 | 60 | 70 |
| average number of plants | 10 | 5 | 10 |
| Gain % | — | 200 | 250 |

The results show that sorbitol, a monosaccharide corresponding to the reduced glucose widely used in the agri-food industry, combined with an elicitor, in particular a xyloglucan, allows a clear improvement in protection.

It was moreover noted that use of the elicitor/sorbitol combination did not result in any interference with the evolution of the plant, given that the development of the elicited plants after the cold stress is comparable with that of the control plants not exposed to the cold.

The invention claimed is:

1. A process for increasing the resistance of vines to cold stress, comprising treating the vines with an eliciting composition comprising a synergistic mixture of:

i) XFGol represented by the following formula:

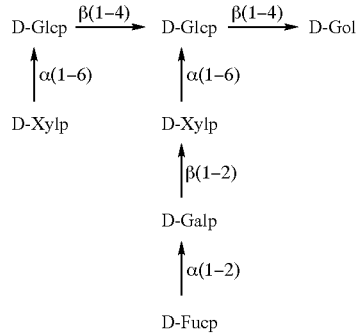

and ii) sorbitol wherein, the XFGol is present at a concentration between 1 nM to 500 nM, and the sorbitol is present at a concentration between 0.05 wt % to 0.5 wt % of the composition.

2. The process according to claim 1, wherein the vines are treated by a method selected from the group consisting of:
   irrigating soil in which the vines are cultivated with the eliciting composition;
   coating seeds from which the vines grow with the eliciting composition; and
   foliar spraying the eliciting composition onto the vines.

3. The process according to claim 1, wherein the vines are *Vitis* genus.

* * * * *

UNITED STATES PATENT AND TRADEMARK OFFICE
CERTIFICATE OF CORRECTION

PATENT NO. : 8,455,461 B2  Page 1 of 1
APPLICATION NO. : 12/674789
DATED : June 4, 2013
INVENTOR(S) : Pascal Salvador It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 358 days.

Signed and Sealed this
Eighth Day of September, 2015

Michelle K. Lee
*Director of the United States Patent and Trademark Office*